(12) United States Patent
Liu (10) Patent No.: US 8,348,920 B2
(45) Date of Patent: *Jan. 8, 2013

(54) DISPOSABLE ABSORBENT ARTICLES HAVING WETNESS APPEARING GRAPHICS

(75) Inventor: Kuang-Kai Liu, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 979 days.

This patent is subject to a terminal disclaimer.

(21) Appl. No.: 10/827,088

(22) Filed: Apr. 19, 2004

(65) Prior Publication Data

US 2005/0234415 A1 Oct. 20, 2005

(51) Int. Cl.
*A61F 13/15* (2006.01)
(52) U.S. Cl. ......................... 604/391; 604/358
(58) Field of Classification Search .................. 604/358, 604/361, 362, 385.01, 391
See application file for complete search history.

(56) References Cited

U.S. PATENT DOCUMENTS

| | | | | |
|---|---|---|---|---|
| 2,254,609 A | * | 9/1941 | Kinzer | 252/408.1 |
| 3,665,923 A | * | 5/1972 | Champaigne, Jr. | 604/364 |
| 3,675,654 A | * | 7/1972 | Baker et al. | 604/361 |
| 4,022,211 A | * | 5/1977 | Timmons et al. | 604/361 |
| 4,249,532 A | * | 2/1981 | Polansky et al. | 604/370 |
| 4,287,153 A | * | 9/1981 | Towsend | 422/56 |
| 4,717,378 A | * | 1/1988 | Perrault et al. | 116/201 |
| 4,738,674 A | | 4/1988 | Todd et al. | |
| 4,744,113 A | | 5/1988 | Kogut | |
| 4,931,051 A | * | 6/1990 | Castello | 604/361 |
| 5,197,958 A | | 3/1993 | Howell | |
| 5,342,861 A | * | 8/1994 | Raykovitz | 523/111 |
| 5,354,289 A | | 10/1994 | Mitchell et al. | |
| 5,389,093 A | * | 2/1995 | Howell | 604/361 |
| 5,458,590 A | * | 10/1995 | Schleinz et al. | 604/361 |
| 5,595,754 A | * | 1/1997 | Ito et al. | 424/443 |
| 5,690,624 A | | 11/1997 | Sasaki et al. | |
| 5,766,212 A | | 6/1998 | Jitoe et al. | |
| 5,834,099 A | | 11/1998 | Steinhardt et al. | |
| 5,902,669 A | | 5/1999 | Steinhardt et al. | |
| 5,947,943 A | | 9/1999 | Lee | |

(Continued)

FOREIGN PATENT DOCUMENTS

BR 0105879-7 A 7/2002

(Continued)

OTHER PUBLICATIONS

Search report for WO 2005/102239 A1, Liu, Nov. 3, 2005, WIPO, A61F 13/42.*

(Continued)

*Primary Examiner* — Tatyana Zalukaeva
*Assistant Examiner* — Benedict L Hanrahan
(74) *Attorney, Agent, or Firm* — Andrew A Paul; John P. Colbert; Dara M. Kendall (57) ABSTRACT

The present invention relates to a disposable absorbent article comprising a liquid pervious topsheet, a liquid impervious backsheet that is at least partially joined to the topsheet, an absorbent core disposed at least partially between the topsheet and the backsheet, and a wetness indicator printed onto a surface of said backsheet wherein the wetness indicator comprises a graphic that further comprises at least one responsive color composition and a varnish coating disposed adjacent to said responsive color composition; wherein upon wetting, said graphic becomes visible to the unaided eye.

16 Claims, 4 Drawing Sheets

U.S. PATENT DOCUMENTS

| | | | |
|---|---|---|---|
| 6,075,178 | A | 6/2000 | La Wilhelm et al. |
| 6,307,119 | B1 | 10/2001 | Cammarota et al. |
| 6,653,522 | B1 * | 11/2003 | Blumenthal et al. .......... 604/361 |
| 6,710,221 | B1 | 3/2004 | Pierce et al. |
| 2003/0164136 | A1 | 9/2003 | Klofta et al. |
| 2004/0064113 | A1 * | 4/2004 | Erdman ........................ 604/361 |
| 2005/0234414 | A1 * | 10/2005 | Liu ............................... 604/361 |

FOREIGN PATENT DOCUMENTS

| | | |
|---|---|---|
| EP | 0 776 645 A1 | 6/1997 |
| EP | 0 813 850 A2 | 12/1997 |
| EP | 1 222 907 A2 | 7/2002 |
| GB | 2 177 977 A | 2/1987 |
| GB | 2 327 354 A | 1/1999 |
| GB | 2 336 112 A | 10/1999 |
| JP | 58-102010 | 6/1983 |
| JP | 58-114772 | 7/1983 |
| JP | 59-024704 U | 2/1984 |
| JP | 60-009907 U | 1/1985 |
| JP | 60-20509 U | 2/1985 |
| JP | 3-221 039 A | 1/1991 |
| JP | 11-004 852 A | 1/1999 |
| JP | 13-327 530 A | 11/2001 |
| JP | 14-282 3014 A | 10/2002 |
| JP | 2004-049405 A | 2/2004 |
| WO | WO 95/00099 A1 | 1/1995 |
| WO | WO 00/76438 A2 | 12/2000 |
| WO | WO 00/76442 A1 | 12/2000 |
| WO | WO 00/76558 A1 | 12/2000 |
| WO | WO 01/41691 A1 | 6/2001 |

OTHER PUBLICATIONS

Search report for WO 2005/102238 A1, Liu, Nov. 3, 2005, WIPO, A61F 13/42.*

Material Safety Data Sheet, Copper Sulfate, International Resources, Inc., Jan. 2001, www.iri-us.com/msds/copper.html.*

Hawley's Condensed Chemical Dictionary, 14th Edition, 2002; definition of fatty acid.*

Hawley's Condensed Chemical Dictionary, 14th Edition, John Wiley & Sons. Inc. (2002), www.knovel.com.*

Available on the Web Archive as of May 12, 2006 [retrieved on Jun. 5, 2009]. Retrieved from the Internet: http://web.archive.org/web/20060512134539/http://www.iri-us.com/msds/copper.html.*

* cited by examiner

DISPOSABLE ABSORBENT ARTICLES HAVING WETNESS APPEARING GRAPHICS

FIELD OF THE INVENTION

The present invention relates to a disposable absorbent article comprising a wetness indicator comprising graphics that appear upon wetting. The graphic further comprises at least one responsive color composition and a varnish coating disposed on top of said responsive color composition. When wetted, with a fluid like urine, the graphic becomes apparent to the unaided eye of a consumer or wearer.

BACKGROUND OF THE INVENTION

More often than not disposable absorbent articles are incorporating graphics as an ordinary feature. In most instances, these graphics are applied to the backsheet of the product so that the graphics are visible while the product is being worn. The graphics have been printed directly on a component of the backsheet or have been printed on a separate layer, such as a tissue layer, which is disposed on the backsheet.

There are many reasons to incorporate graphics in disposable absorbent articles. For instance, the graphics can improve the appearance and appeal of the product, to both the wearer and the purchaser. Graphics can also impact the manner in which a disposable absorbent article is used. For example, graphics on disposable diapers can be used by caregivers to amuse and/or educate a child during diapering. Similarly, graphics on disposable training pants can provide educational and motivational mechanisms to facilitate the toilet training process. Graphics on training pants can also serve to increase the child's interest in the product and thereby increase the child's interest in the toilet training process.

Graphics can further be used to indicate when a urine insult has occurred. For instance, it has been known in the art that upon wetting, disposable absorbent articles like diapers have included graphics that appear or disappear to indicate the insult. To date, however, it has not been possible to deliver disposable absorbent products which include printed graphics that can be disposed directly onto a film portion of the backsheet of an absorbent product and have the graphic ultimately appear clearly to the unaided eye of a consumer and wearer when exposed to liquid.

SUMMARY OF THE INVENTION

The present invention, therefore, relates to disposable absorbent articles comprising:
a) a liquid pervious topsheet;
b) a liquid impervious backsheet that is at least partially joined to the topsheet;
c) an absorbent core disposed at least partially between the topsheet and the backsheet; and
d) a wetness indicator printed onto a surface of said backsheet; the wetness indicator comprising a graphic that further comprises at least one responsive color composition and a varnish coating disposed adjacent to said responsive color composition;
wherein upon wetting, said graphic becomes visible to the unaided eye.

DETAILED DESCRIPTION OF THE DRAWINGS

FIG. 1 illustrates a flat out view of an absorbent article of the present invention prior to wetting. In this embodiment, the article is a diaper comprising a liquid pervious topsheet 16, a liquid impervious backsheet 24 that is at least partially joined to the topsheet, an absorbent core 22 disposed at least partially between the topsheet and the backsheet, and a wetness indicator 26 printed onto a surface of the backsheet; the wetness indicator comprising a graphic 18 that further comprises at least one responsive color composition and a varnish coating 14 disposed adjacent to the responsive color composition; wherein when wetted, the graphic becomes visible to the unaided eye.

DETAILED DESCRIPTION OF THE INVENTION

Definitions

Figure 1:
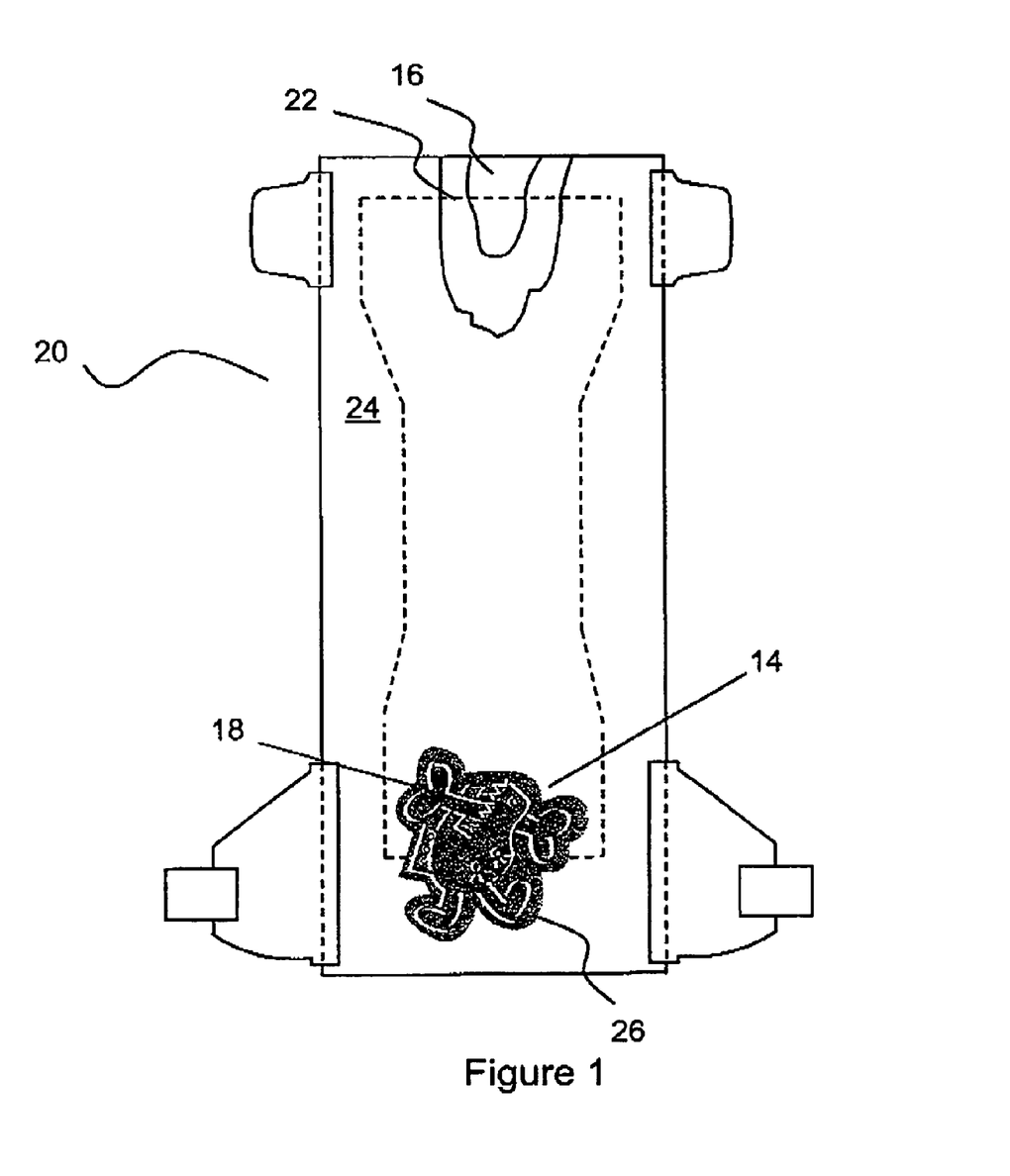
Figure 2:
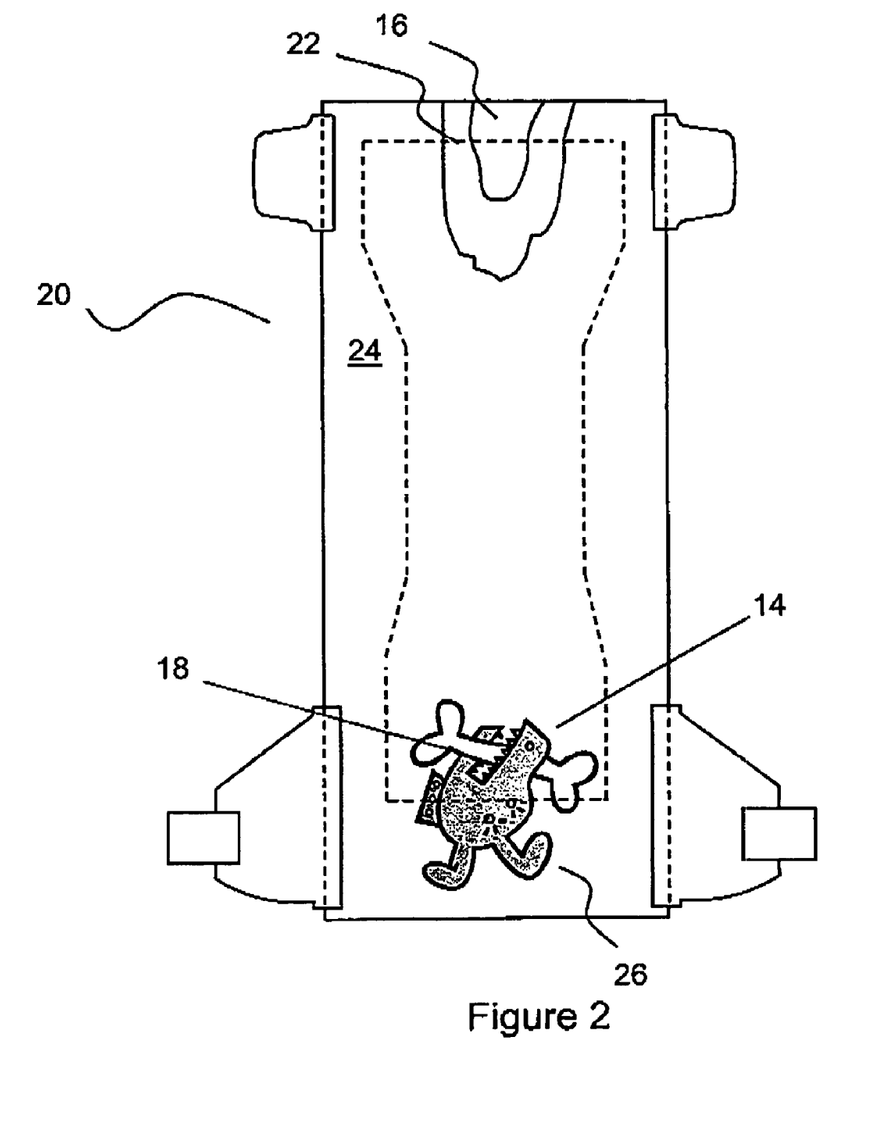
FIG. 2 illustrates the absorbent article of FIG. 1 after wetting wherein the graphic becomes visible to the unaided eye.
Figure 3:
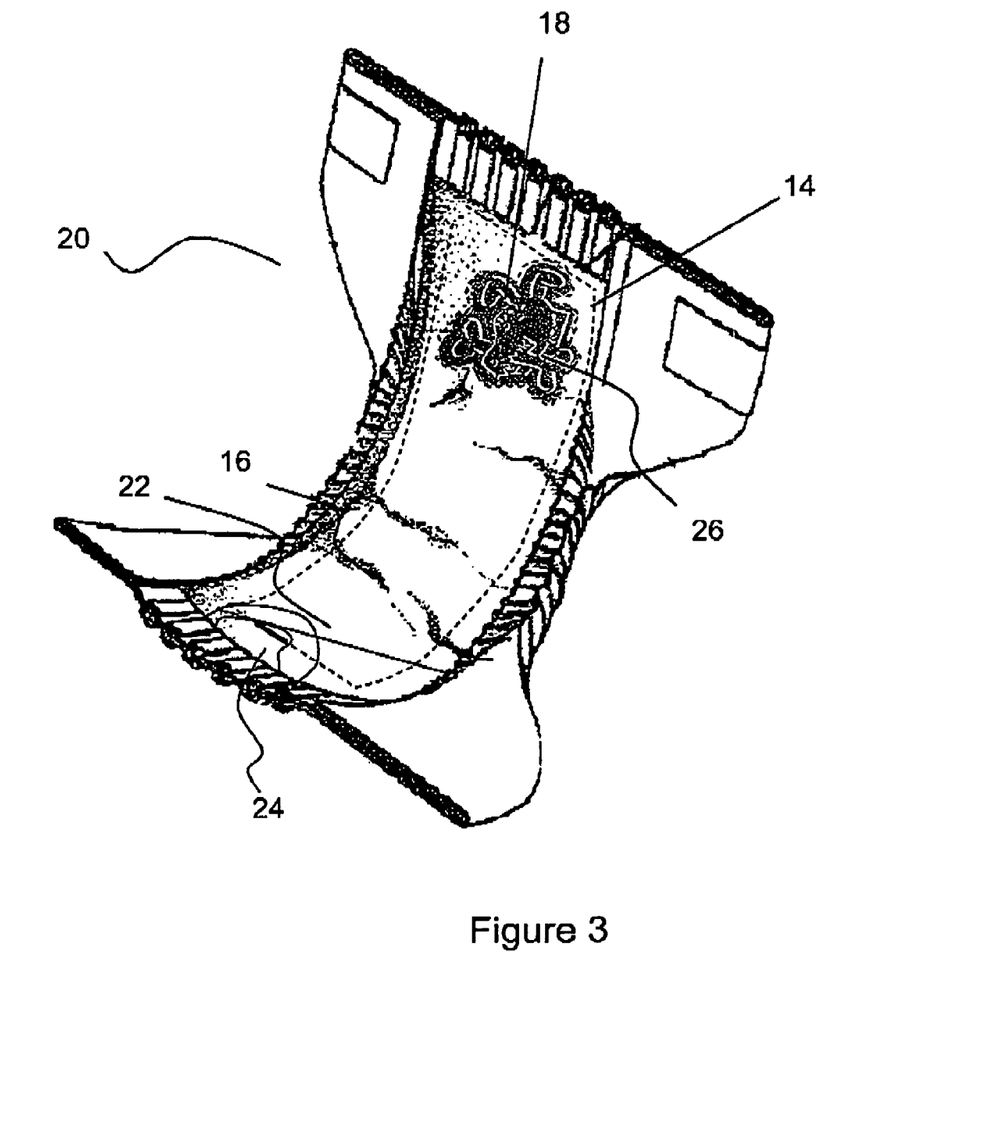
FIG. 3 illustrates a perspective view of a further embodiment of an absorbent article of the present invention prior to wetting.
Figure 4:
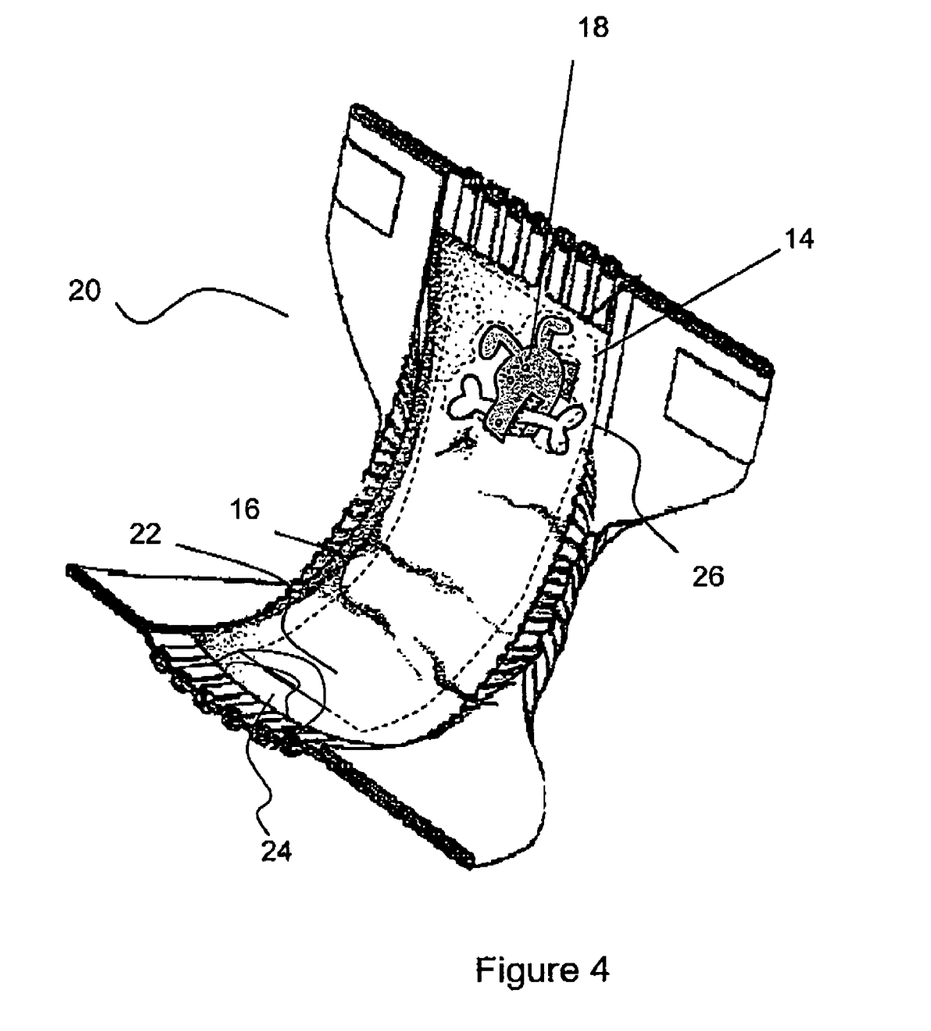
FIG. 4 illustrates a perspective view the absorbent article of FIG. 3 after wetting wherein the graphic becomes visible when contacted with fluid.

As used herein, the term "absorbent articles" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

As used herein, the term "absorbent core" refers to the component of the absorbent article that is primarily responsible for fluid handling properties of the article, including acquiring, transporting, distributing and storing body fluids. As such, the absorbent core typically does not include the topsheet, backsheet or outer cover of the absorbent article.

As used herein, the term "bonded" refers to different materials being attached (cohesively or adhesively) in at least a portion thereof. The attached portions may be random or may have a pattern such as stripes, spirals, dots, and the like. The attached portions may be located at the peripheries, throughout the surface area, or both. Suitable attachment means known in the art may be used, including but not limited to adhesives, heat, pressure, crimping, ultrasonic, chemical (via hydrogen bonds or other cohesive forces), mechanical (e.g., fasteners, entanglements), hydraulic, vacuum and combinations thereof.

As used herein, the term "composite structure" refers to a multi-region structure wherein the materials comprising the regions may be operatively associated or bonded. The regions may even be in intimate contact such that the composite has a unitary structure. Further, the regions may be positioned in a layered (face-to-face) arrangement, or a side-by-side arrangement.

As used herein, the term "disposable" is used in its ordinary sense to mean an article that is disposed or discarded after a limited number of usage events over varying lengths of time, preferably less than about 20 events, more preferably less than about 10 events, even more preferably less than about 5 events, and most preferably less than about 2 events.

As used herein, the term "intimate bonding" refers to physical contact between two layers such that they resist separation with no readily visually identifiable areas of separation. In one particular embodiment, the inner and outer layers are adhesively laminated together in the graphic regions using a meltblowing process to form an overlapping network of adhesive filaments.

As used herein, the term "joined" encompasses configurations wherein an element is directly secured to the other element by affixing the element directly to the other element, and configurations wherein the element is indirectly secured to the other element by affixing the element to intermediate member(s), which in turn are affixed to the other element.

The term "macroporous" refers to materials having pores too large to effect capillary transport of fluid, generally having pores greater than about 0.5 mm in diameter and, more specifically, having pores greater than about 1.0 mm in diameter.

As used herein, the terms "meltblown" and "meltblown web" refer to a web having fibers formed by extruding a molten thermoplastic material through a plurality of fine, usually circular, die capillaries as molten threads or filaments into converging high velocity heated gas/air streams which attenuate the molten filaments to reduce their diameter. The reduction in fiber diameter is substantially greater then the reduction of fiber diameter in the spunbonding process, resulting in microfibers having average fiber diameter larger than 0.2 microns and typically in the range of 0.6 to 10 microns. Thereafter, the meltblown fibers are carried by the high velocity gas stream and are deposited on a collecting surface to form a web of randomly disbursed fibers. Various meltblown processes are known in the art.

As used herein, the term "microporous" refers to materials which are capable of transporting fluids by capillary action.

As used herein, the terms "nonwoven" and "nonwoven web" refers to a web that has a structure of individual fibers which are interlaid forming a matrix, but not in an identifiable repeating manner. Nonwoven webs may be formed by a variety of processes known to those skilled in the art, for example, meltblowing, spunbonding, wet-laying, air-laying, and various bonding-carding processes.

As used herein, the term "operatively associated" refers to a structure comprising different materials positioned at least in partial contact with each other in use. The materials are physically separable and each exhibits properties that can be measured individually. The materials may be arranged in a face-to-face relationship in the z-dimension, or in a side-by-side relationship in the xy-dimension.

As used herein, the term "pulp" or "cellulosic fibers" include those natural fiber derived from trees or vegetations (e.g., hardwood fibers, softwood fibers, hemp, cotton, flax, esparto grass, milkweed, straw, bagasse and the like), their processed/regenerated fibers (e.g., Rayon®) or chemically derivatized fibers (e.g., cellulose esters), and combinations thereof. Suitable hardwood fibers include eucalyptus fibers. Suitable hardwood fibers may be prepared by kraft or other chemical pulping methods. Suitable softwood fibers include southern softwood (SS) fibers and northern softwood (NS) fibers. Softwood fibers for use herein can be chemically (e.g., without limitation, kraft pulp) or mechanically pulped (e.g., without limitation, chemithermal mechanical pulp (CTMP) and thermal mechanical pulp (TMP)).

As used herein, the term "region" refers to a zone or an area comprising a material being physically, chemically, or visually distinguishable from surrounding or adjoining materials. Various regions of materials may include transitional regions in between. The regions may be positioned in the z-dimension or in the xy-dimension. As used herein, the term "z-dimension" refers to the dimension orthogonal to the length and width of the structure or article. The z-dimension usually corresponds to the thickness of the structure or article. As used herein, the term "xy-dimension" refers to the plane orthogonal to the thickness of the member, core or article when the member, core or article is in a flat-out state. The xy-dimension usually corresponds to the length and width, respectively, of the structure or article in a flat-out state.

As used herein, the terms "spunbond" and "spunbonded web" refers to a web having fibers formed by extruding a molten thermoplastic material as filaments from a plurality of fine capillaries of a spinnerette having a circular or other configuration, then rapidly reducing the diameter of the extruded filaments by fluid drawing or other well known spunbonding mechanisms. Spunbond fibers are quenched and generally not tacky when they are deposited onto a collecting surface. Spunbond fibers are generally continuous and often have average between about 10 to about 30 microns.

As used herein, the term "unitary structure" refers to a structure comprising materials having different characteristics joined together to form an integral entity such that the materials are substantially inseparable physically, and the unitary structure exhibits properties resulting from the combination of the materials therein. The materials may be arranged in a face-to-face relationship in the z-dimension, or in a side-by-side relationship in the xy-dimension.

The following detailed description is directed toward absorbent articles. It is, however, likely that the disclosed articles could be modified such that the overall concept discussed herein could likewise be applied to use in other hygiene or health care products, such as bandages, dressings, wipes, bibs, surgical drapes, surgical gowns, and the like.

Absorbent Article

The absorbent articles of the present invention comprise a liquid pervious topsheet, a liquid impervious backsheet that is at least partially joined to the topsheet, an absorbent core disposed at least partially between the topsheet and the backsheet, and a wetness indicator printed onto a surface of said backsheet; the wetness indicator comprising a graphic that further comprises at least one responsive color composition and a varnish coating disposed adjacent to said responsive color composition; wherein upon wetting, said graphic becomes visible to the unaided eye.

In certain embodiments, the absorbent articles may additionally include one or more components selected from the group consisting of an outer cover, side panels, a cuff, an elastic feature, a fastening system, and combinations thereof.

The main body of an absorbent article, e.g., a diaper, comprises at least the absorbent core, and the topsheet. An outer cover forms the chassis, onto which other components of the diaper are added to form the unitary structure of the diaper. In alternative embodiments, the article may be preformed by the manufacturer to create a pant. The term "pant", as used herein, refers to disposable garments having a waist opening and leg openings designed for infant or adult wearers. A pant may be placed in position on the wearer by inserting the wearer's legs into the leg openings and sliding the pant into position about the wearer's lower torso. A pant may be preformed by any suitable technique including, but not limited to, joining together portions of the article using refastenable and/or non-refastenable bonds (e.g., seam, weld, adhesive, cohesive bond, fastener, etc.). While the term "pant" is used herein, pants are also commonly referred to as "closed diapers", "prefastened diapers", "pull-on diapers", "training pants" and "diaper-pants". Suitable pants are disclosed in U.S. Pat. Nos. 5,246,433; 5,569,234, 6,120,487, 6,120,489, 4,940,464, 5,092,861, 5,897,545, 5,957,908, and U.S. patent Publication 2003/0233082A1.

Topsheet

The absorbent articles of the present invention comprise a topsheet. The topsheet is preferably compliant, soft feeling, and non-irritating to the wearer's skin. It can be elastically stretchable in one or two directions. Further, the topsheet is liquid pervious, permitting liquids (e.g., menses, urine, and/or runny feces) to readily penetrate through its thickness. A suitable topsheet can be manufactured from a wide range of materials such as woven and nonwoven materials; apertured or hydroformed thermoplastic films; porous foams; reticulated foams; reticulated thermoplastic films; and thermoplastic scrims. Suitable woven and nonwoven materials may comprise of natural fibers such as wood or cotton fibers; synthetic fibers such as polyester, polypropylene, or polyethylene fibers; or combinations thereof. If the topsheet includes fibers, the fibers may be spunbond, carded, wet-laid, melt-blown, hydroentangled, or otherwise processed as is known in the art. One suitable topsheet comprising a web of staple-length polypropylene fibers is manufactured by Veratec, Inc., a Division of International Paper Company, of Walpole, Mass. under the designation P-8.

Preferred topsheet for use in the present invention are selected from high loft nonwoven topsheets and apertured film topsheet. Apertured film topsheet typically are pervious to bodily exudates, yet non-absorbent, and have a reduced tendency to allow fluids to pass back through and rewet the wearer's skin. Suitable apertured films include those described in U.S. Pat. Nos. 5,628,097, 5,916,661, 6,545,197, 6,107,539, and PCT Patent Publication WO 00/69382 A2.

Further, suitable topsheet materials for depositing solid excretions thereon may include nonwovens having apertures, which are at least in the portions that are aligned with the feces deposition region of the article. Suitable apertured nonwovens are described in more detail in U.S. Pat. Nos. 6,414, 215, 5,342,338, and 5,941,864 and U.S. patent Publication 2002/017376. In another embodiment of feces handling articles, such topsheets can be combined with feces handling members, e.g., underlying such topsheets, and which are further described in the abovementioned patent documents.

Suitable formed film topsheets are described in U.S. Pat. Nos. 3,929,135, 4,324,246, 4,342,314, 4,463,045, 5,006,394. Other suitable topsheets may be made in accordance with U.S. Pat. Nos. 4,609,518 and 4,629,643. Such formed films are available from The Procter & Gamble Company of Cincinnati, Ohio as "DRI-WEAVE" and from Tredegar Corporation, based in Richmond, Va., as "CLIFF-T."

Preferably, at least a portion of the topsheet is made of a hydrophobic material or is treated to be hydrophobic in order to isolate the wearer's skin from liquids contained in the absorbent core. If the topsheet is made of a hydrophobic material, preferably at least a portion of the upper surface of the topsheet is treated to be hydrophilic so that liquids will transfer through the topsheet more rapidly. The topsheet can be rendered hydrophilic by treating it with a surfactant or by incorporating a surfactant into the topsheet. Suitable methods for treating the topsheet with a surfactant include spraying the topsheet material with the surfactant and/or immersing the material into the surfactant. A more detailed discussion of such a treatment and hydrophilicity is contained in U.S. Pat. Nos. 4,988,344, 4,988,345, and 4,950,254. A more detailed discussion of some suitable methods for incorporating a surfactant in the topsheet 24 can be found in U.S. Statutory Invention Registration No. H1670. Alternatively, the topsheet may include an apertured web or film which is hydrophobic. This may be accomplished by eliminating the hydrophilizing treatment step from the production process and/or applying a hydrophobic treatment to the topsheet, such as a polytetraflouroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet may be coated with a lotion as is known in the art. Examples of suitable lotions include those described in U.S. Pat. Nos. 5,607,760, 5,609,587, 5,635,191, 5,643,588, and 5,968,025. The lotion may function alone or in combination with another agent as the hydrophobizing treatment described above. The topsheet may also include or be treated with antibacterial agents, some examples of which are disclosed in PCT Publication No. WO 95/24173. Further, the topsheet, the outer cover or any portion of the topsheet or outer cover may be embossed and/or matte finished to provide a more cloth like appearance.

The topsheet may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" (from the article) is increased. Typically, the aperture should have an area of between about 10 $cm^2$ and about 50 $cm^2$. The aperture preferably has an area of between about 15 $cm^2$ and 35 $cm^2$.

Further, the topsheet may be fully or partially elasticated or may be foreshortened so as to provide a void space between the topsheet and the core. Exemplary structures including elasticized or foreshortened topsheets are described in more detail in U.S. Pat. Nos. 4,892,536, 4,990,147, 5,037,416, and 5,269,775.

Backsheet

The backsheet is preferably impervious to fluids (e.g., menses, urine, and/or runny feces) and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, and/or composite materials such as a film-coated nonwoven material (i.e., having an inner film layer and an outer nonwoven layer). A suitable backsheet is a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet is preferably embossed and/or matte-finished to provide a more clothlike appearance. Further, the backsheet may permit vapors to escape from the absorbent core (i.e., the backsheet is breathable) while still preventing exudates from passing through the backsheet. The size of the backsheet is dictated by the size of the absorbent core and the exact absorbent article design selected.

The backsheet and the topsheet are positioned adjacent a garment surface and a body surface, respectively, of the absorbent core. The absorbent core is preferably joined with the topsheet, the backsheet, or both in any manner as is known by attachment means such as those well known in the art. However, embodiments of the present invention are envisioned wherein portions of the entire absorbent core are unattached to one or both of the topsheet and the backsheet.

For example, the backsheet and/or the topsheet may be secured to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986. An exemplary attachment means of an open pattern network of filaments comprises several lines of adhesive filaments swirled into a spiral pattern such as illustrated by the apparatus and method shown in U.S. Pat. Nos. 3,911,173, 4,785,996 and 4,842,666. Alternatively, the attachment means may comprise heat bonds, pressure bonds, ultrasonic bonds, dynamic mechanical bonds, or any other suitable attachment means or combinations of these attachment means as are known in the art.

The backsheet preferably includes an inner and outer layer, each of which can be bonded to the other by a variety of means known in the art, including thermal bonds, adhesive bonds, ultrasonic lamination, or the like. Intimate bonding of the inner and outer layers in the graphic regions reduces light diffraction and thus improves the brightness and overall visibility of the wetness indicator graphic. Adhesive bonding can also be accomplished using adhesive slot coating, high frequency oscillation patterns, for example in swirl or spray patterns, and other fine denier and/or high coverage application techniques. Suitable laminate adhesives, which can be applied continuously or intermittently, can be obtained from Findley Adhesives, Inc. or from National Starch and Chemical Company.

The outer layer of the backsheet can be made in a variety of forms using different processes. For example, the outer layer may be formed as a carded web, a bonded carded web, a spunbond web, a needled fabric, a woven fabric, or the like to provide a generally cloth-like texture to the wearer. Other additives such as titanium dioxide can represent about 0.5% or less, particularly about 0.3% or less, of the outer layer. In one particular embodiment, the outer layer comprises a spunbond web formed of about 99.5 to 100% polypropylene resin and about 0.5% or less other additives. The outer layer is desirably a lightweight material having a basis weight of about 15 to about 30 gsm and more preferably from about 15 to about 25 gsm.

Absorbent Core

The articles of the present invention additionally comprise one or more absorbent cores. The absorbent core is at least partially disposed between the topsheet and the backsheet and may take on any size or shape that is compatible with the disposable absorbent article. Exemplary absorbent structures for use as the absorbent core of the present invention that have achieved wide acceptance and commercial success are described in U.S. Pat. Nos. 4,610,678, 4,673,402, and 4,888,231, and 4,834,735. The absorbent core may further comprise the dual core system containing an acquisition/distribution core of chemically stiffened fibers positioned over an absorbent storage core as detailed in U.S. Pat. Nos. 5,234,423 and 5,147,345.

In general, the absorbent core is capable of absorbing or retaining liquids (e.g., menses, urine, and/or other body exudates). The absorbent core is preferably compressible, conformable, and non-irritating to the wearer's skin. The absorbent core may be manufactured in a wide variety of sizes and shapes (e.g., rectangular, oval, hourglass, "T" shaped, dog bone, asymmetric, etc.). The absorbent core may include any of a wide variety of liquid-absorbent materials commonly used in absorbent articles, such as comminuted wood pulp, which is generally referred to as airfelt. Examples of other suitable absorbent materials for use in the absorbent core include creped, cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

As discussed herein "absorbent gelling materials" and "superabsorbent polymers" are those materials that, upon contact with aqueous fluids, such as bodily fluids, imbibes such fluids and form hydrogels. These absorbent gelling materials are typically capable of absorbing large quantities of aqueous bodily fluids, and further capable of retaining such absorbed fluids under moderate pressures. These absorbent gelling materials are typically in the form of discrete, nonfibrous particles. Other forms, such as fibers, foams, sheets, strips, or other macrostructures, are also suitable for use herein. Suitable absorbent gelling materials in the form of open cell foams may include those disclosed in U.S. Pat. Nos. 3,563,243, 4,554,297, 4,740,520, and 5,260,345.

The configuration and construction of the absorbent core may also be varied (e.g., the absorbent core may have varying caliper zones and/or have a profile so as to be thicker in the center; hydrophilic gradients; superabsorbent gradients; or lower average density and lower average basis weight zones, e.g., acquisition zones; or may comprise one or more layers or structures). The total absorbent capacity of the absorbent core should, however, be compatible with the design loading and the intended use of the absorbent article. Further, the size and absorbent capacity of the absorbent core may be varied to accommodate different uses such as diapers, incontinence pads, pantiliners, regular sanitary napkins, and overnight sanitary napkins, and to accommodate wearers ranging from infants to adults. The absorbent core can include other absorbent components that are often used in absorbent articles, for example, a dusting layer, a wicking or acquisition layer, or a secondary topsheet for increasing the wearer's comfort.

In certain embodiments of the present invention, the absorbent article may also include a sublayer disposed between the topsheet and the backsheet. The sublayer may be any material or structure capable of accepting, storing or immobilizing bodily exudates. Thus, the sublayer may include a single material or a number of materials operatively associated with each other. Further, the sublayer may be integral with another element of the absorbent article or may be one or more separate elements joined directly or indirectly with one or more elements of the article. Further, the sublayer may include a structure that is separate from the core or may include or be part of at least a portion of the core.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga.

Other suitable absorbent and nonabsorbent sublayers are described in U.S. Pat. Nos. 6,680,422 and 5,941,864. Further, the sublayer, or any portion thereof, may include or be coated with a lotion or other known substances to add, enhance or change the performance or other characteristics of the element.

Wetness Indicator

The disposable absorbent articles of the present invention further comprise a wetness indicator printed onto a film surface of said backsheet. The wetness indicator comprises a graphic that further comprises at least one responsive color composition and a varnish coating disposed adjacent to said responsive color composition. In most embodiments, the graphic is hidden from view prior to wetting as it is minimally visible (i.e., transparent) and it typically assumes the color of the backsheet on which it is printed. Upon wetting, however, the graphic becomes visible to the unaided eye.

According to the present invention, the responsive color composition comprises from about 1% to about 10%, by weight of the composition, of fluid dyestuff, more preferably from about 2% to about 8%, and most preferably from about 3% to about 7%.

Suitable fluid dyestuffs include water soluble ink colorants like direct dyes, acid dyes, base dyes, and various solvent soluble dyes. Examples include, but are not limited to, C.I. Acid Yellow 73, C.I. Solvent Yellow 94, C.I. Acid Yellow 74, C.I. Solvent Orange 32, C.I. Solvent Red 42, C.I. Acid Orange 11, C.I. Solvent Red 72, C.I. Pigment Orange 39, C.I. Solvent Orange 18, C.I. Acid Red 87, C.I. Solvent Red 43, C.I. Pigment Red 90:1, C.I. Solvent Red 44, C.I. Solvent Red 45, C.I. Solvent Orange 16, C.I. Acid Red 91, C.I. Acid Red 98, C.I. Acid Red 92, C.I. Solvent Red 48, C.I. Pigment Red 174, C.I. Acid Red 95, C.I. Solvent Red 73, C.I. Pigment Red 191, C.I. Acid Red 51, C.I. Food Red 14, C.I. Pigment Red 172, C.I. Solvent Red 140, C.I. Acid Red 93, C.I. Solvent Red 47, C.I. Acid Red 94, C.I. Solvent Red 141, C.I. Mordant Violet 25, C.I. Solvent Orange 17, C.I. Solvent Red 46, D&C Red 27(C.I. 45410:1), D&C Orange 5(C.I. 45370:2), and combinations thereof. More preferred fluid dyestuffs are selected from the group consisting of D&C Red 27, D&C Orange 5, and combinations thereof.

Without being limited by theory, the inventors believe that upon contact with fluid the below described varnish coating partially solubilizes and forms cracks in the coating. The liquid penetrates these cracks and then reacts with a lactone base of the responsive color composition (or ink) to form a carboxylic acid which in turn results in the appearance of the final color. The figure below exemplifies this reaction, known in the art as a hydrolysis reaction.

The solvents of the present invention are preferably non-aqueous solvents. Preferred non-aqueous solvents may comprise alcohols, acetates, and combinations thereof. The alcohol solvents are preferably selected from the group consisting of iso-propyl alcohol, n-propyl alcohol, ethanol, methanol, and combinations thereof. Likewise, suitable acetate solvents include, but are not limited to, isopropyl acetate, n-propyl acetate, and combinations thereof. The responsive color composition preferably comprises from about 10% to about 99%, by weight of the composition, of the solvent. More preferably, the responsive color composition comprises from about 30% to about 80% of a solvent and even more preferably from about 40% to about 75%.

An exemplary responsive color composition is an ink that is commercially available from Osaka Printing Industries as Omutsu-you-A ICA pants (translated from Japanese).

Varnish Coating

The responsive color composition of the present invention is disposed adjacent to a varnish coating. Without being limited by theory, this coating serves as a sealant of sorts for the responsive color composition. Upon contact with an aqueous liquid, the graphic is then able to be visible to the unaided eye as the varnish coating which is partially solubilized by the liquid creates cracks or entry points in the coating which then allows the liquid to contact the responsive color composition. Upon contact with the liquid, the color responsive color compositions (both first and second) begin to exhibit the intended color that forms the graphic. Suitable materials for the varnish coating may be selected from the group consisting of acrylic copolymers, shellac-based acrylic resins, polyamides, and combinations thereof. These materials are intended to be exemplary but not limiting in any way. Additionally, the varnish coating may be disposed over the graphic formed by the responsive color composition, beneath the graphic, or both. Moreover, it is preferred that the varnish coating be disposed adjacent to the graphic such that one or more edges of the coating extend at least about 25% past one or more edges of the graphic. More preferably, the varnish coating extends at least about 15% and most preferably at least about 10% past one or more edges of the graphic.

Backsheet graphics are directly visible on the exterior surface of the absorbent article and have been extremely appealing to children. Moreover, parents and caregivers can use such wetness indicator graphics as educational and motivational tools to advance the toilet training process. Thus, the wetness indicator graphics are suitably disposed on the backsheet via printing methods. The term "disposed" and variations thereof are intended to mean that one element can be integral with another element, or that one element can be a separate structure bonded to or placed with or placed near another element. Thus, the graphics can be formed or applied directly or indirectly to a surface of the outer cover, formed or applied between layers of a multiple layer outer cover, formed or applied to a substrate that is placed with or near the outer cover, formed or applied within a layer of the outer cover or another substrate, or other variations or combinations thereof.

In preferred embodiments, the graphics can be printed (via flexography, gravure, digital printing, etc.). For such printing, it is envisioned that a multiplicity of additional responsive color compositions may be utilized such that multicolor graphics are achieved upon wetting of the article. Regardless of the type of printing method employed, preferred speeds for printing range from about 50 m/min to about 500 m/min, preferably from about 100 m/min to about 300 m/min. In preferred embodiments, the printing speed is set at about 200 m/min. Additionally a multicolor print press is utilized to print the graphic on the backsheet material with the color composition and varnish coating being printed in succession from different print stations.

Additionally, other graphics may be sprayed or otherwise applied directly on a layer of the backsheet. For instance, in other embodiments, the graphics can be applied to a layer placed with or near the backsheet, such as a substrate associated with the absorbent assembly, including but not limited to tissue layers, liquid handling layers, absorbent layers, or the like.

The graphics for use with the present invention can be located on or against either surface (i.e., garment-facing (aka exterior) surface or body-facing (aka interior) surface) of the backsheet provided the graphics remain visible from the exterior of the product when wetted. In preferred embodiments, the wetness indicator graphic is printed on the interior surface of the backsheet.

The wetness indicator can be in liquid communication with the absorbent assembly of the product. As used herein, the term "liquid communication" means that liquid such as urine is able to travel from one layer or element to another layer or element. The absorbent assembly can but need not include a slot or densified region, incorporate a liquid distribution layer, or the like, to channel or direct liquid to the location near the backsheet and/or outer cover where the graphics are located.

Absorbent articles suitable for use as the present invention include diapers, training pants, incontinence products, diaper pants, disposable underwear, or the like. Suitable training pants and diaper pants can have seamed side portions or refastenable side portions. The present invention is particularly suited for use with training pants or diaper pants to aid in toilet training. Particular diapers and training pants suitable for use with the present invention are disclosed in U.S. Pat. Nos. 3,860,003, 4,636,207, 4,695,278, 4,704,115, 4,795,454, 4,900,317, 4,909,803 (Reissued as U.S. Pat. No. RE34920), U.S. Pat. Nos. 5,085,654, 5,492,751, 6,476,288, 6,627,787, 5,507,760, 5,609,587, 5,635,191, 5,643,588, 6,118,041, SIR H1630, U.S. Pat. Nos. 5,246,433, 5,769,838, 5,899,895, 5,899,896, and 6,120,487. Additional patents discussing suitable training pants are disclosed earlier herein.

In a preferred embodiment, the absorbent article further comprises at least a first cuff for providing improved containment of liquids and other body exudates; an elastic waist feature that provides improved fit and containment; and a fastening system which forms a side closure which maintains the first waist region and the second waist region in an overlapping configuration such that lateral tensions are maintained around the circumference of the absorbent article to maintain the absorbent article on the wearer. The absorbent article may also comprise elasticized side panels (not shown) in the waist regions and to provide an elastically extensible feature that provides a more comfortable and contouring fit and more effective application of the absorbent article.

The "elasticized" leg cuffs can be constructed in a number of different configurations, including those described in U.S. Pat. Nos. 3,860,003, 4,636,207, 4,695,278, 4,704,115, 4,795,454, 4,900,317, 4,909,803 (Reissued as U.S. Pat. No. RE34920), U.S. Pat. Nos. 5,085,654, 5,492,751, 6,476,288 and SIR H1630.

For example, the absorbent article may include one ore more first cuffs that provide improved containment of liquids and other body exudates. First cuffs may also be referred to as outer leg cuff, leg bands, side flaps, leg cuffs or elastic cuffs. U.S. Pat. No. 3,860,003 describes a disposable diaper which provides a contractible leg opening having a side flap and one or more elastic members to provide an elasticized leg cuff.

Additionally, an absorbent article of the present invention may include one or more second cuffs that also provide improved containment of liquids and other body exudates. Second cuffs may also be referred to as barrier leg cuffs, inner leg cuffs or "stand-up" elasticized flaps. U.S. Pat. Nos. 4,808,178 and 4,909,803 (Reissued as U.S. Pat. No. RE34920) describe disposable diapers having "stand-up" elasticized flaps that improve the containment of the leg regions.

First cuff and second cuff may both be provided by way of a dual cuff, as exampled in U.S. Pat. Nos. 4,695,278 and 4,795,454. Additional cuffs may be provided in an article of the present invention as detailed in US Statutory Invention Registration H1630.

Another component that may be included in the articles or composites of the present invention is a hydrophobic surface coating as disclosed in copending U.S. provisional application Ser. No. 60/543,785 (P&G Case 9528P). This hydrophobic surface coating may be paired with the barrier coating of the present invention on the barrier layer or may be disposed adjacent to one or more additional components of the absorbent articles or composites of the present invention. For instance, this hydrophobic surface coating may be disposed on an interior surface of one or more leg cuffs, waist portions, or other areas of the absorbent article.

All documents cited in the Detailed Description of the Invention are, in relevant part, incorporated herein by reference; the citation of any document is not to be construed as an admission that it is prior art with respect to the present invention.

EXAMPLES

Example 1

An absorbent article that includes a wetness indicator according to the present invention is produced as follows. A breathable polyolefin film is selected from either of BR-120 and BR-121, which are commercially available from Clopay of Cincinnati, Ohio. Each of these films has a breathability of 1500 to 4000 MVTR and basis weight of 28 gsm and may serve as the material on which printing occurs. A Windmoller & Holscher Olympia 736 ST 6 color printing machine or the equivalent Flexo printer is loaded with 2 separate wetness indicator inks. The first wetness indicator ink is a varnish coating that contains 20±5 wt % of shellac and 60±10 wt % of isopropyl alcohol and 5-10 wt % of hydroxypropyl cellulose and silica. The second wetness indicator ink is a responsive color composition that contains 3±1 wt % D&C red 27, 60±10 wt % isopropyl alcohol, 5-10 wt % silica and hydroxrpropyl cellulose. The film is first printed with the varnish coating at a 3 g/sqm add-on weight and at a line speed of 100 m/min. The varnish coating is printed on an area that is 20±5% larger in area than the graphic design that is printed with the second wetness indicator ink so that the varnish coating completely covers the second wetness indicator ink graphic during the print process variation.

This film is then dried and wound on to a roll and stored. At this time the printed varnish coating and second wetness indicator ink graphic are completely invisible to naked eyes. This film is then incorporated into any one of the absorbent articles disclosed in U.S. Pat. Nos. 3,860,003, 4,636,207, 4,695,278, 4,704,115, 4,795,454, 4,900,317, 4,909,803 (Reissued as U.S. Pat. No. RE34920), U.S. Pat. Nos. 5,085,654, 5,492,751, 6,476,288, 6,627,787, 5,507,760, 5,609,587, 5,635,191, 5,643,588, 6,118,041, SIR H1630, U.S. Pat. Nos. 5,246,433, 5,769,838, 5,899,895, 5,899,896, and 6,120,487. Upon wetting of such an absorbent article, after about one minute an image begins to appear on the article's backsheet surface that faces the garment. After about 5 minutes, a bright pink image appears clearly.

Example 2

An absorbent article that includes a wetness indicator according to the present invention is produced as follows. A breathable polyolefin film is selected from either of BR-120 and BR-121, which are commercially available from Clopay of Cincinnati, Ohio. Each of these films has a breathability of 1500 to 4000 MVTR and basis weight of 28 gsm and may serve as the material on which printing occurs. A Windmoller & Holscher Olympia 736 ST 6 color printing machine or the equivalent Flexo printer is loaded with 2 separate wetness indicator inks. The first ink is a responsive color composition that includes 3±1 wt % D&C red 27 and 60±10 wt % isopropyl alcohol. The second wetness indicator ink is a varnish coating that contains 20±5 wt % of shellac, 60±10 wt % of isopropyl alcohol and 5-10 wt % of hydroxypropyl cellulose and silica. The film is first printed with the responsive color composition at a 3 g/sqm add-on weight and at a line speed of 100 m/min. The varnish coating is added on at the same rate but is printed on an area that is 20±5% larger than the responsive color composition graphic that is printed with the first ink so that the varnish coating completely covers the wetness ink during print process variation.

This film is then dried and wound on to a roll and stored. At this time the printed varnish coating and responsive color composition graphic are completely invisible to naked eyes. This film is then incorporated into any one of the absorbent articles disclosed in U.S. Pat. Nos. 3,860,003, 4,636,207, 4,695,278, 4,704,115, 4,795,454, 4,900,317, 4,909,803 (Reissued as U.S. Pat. No. RE34920), U.S. Pat. Nos. 5,085,654, 5,492,751, 6,476,288, 6,627,787, 5,507,760, 5,609,587, 5,635,191, 5,643,588, 6,118,041, SIR H1630, U.S. Pat. Nos. 5,246,433, 5,769,838, 5,899,895, 5,899,896, and 6,120,487. Upon wetting of such an absorbent article, after about one minute an image begins to appear on the article's backsheet surface that faces the garment. After about 5 minutes, a bright pink image appears clearly.

Example 3

An absorbent article that includes a wetness indicator according to the present invention is produced as follows. A breathable polyolefin film is selected from either of BR-120 and BR-121, which are commercially available from Clopay of Cincinnati, Ohio. Each of these films has a breathability of 1500 to 4000 MVTR and basis weight of 28 gsm and may serve as the material on which printing occurs. A Windmoller & Holscher Olympia 736 ST 6 color printing machine or the equivalent Flexo printer is loaded with 3 separate wetness indicator inks. The first wetness indicator ink is a varnish coating that contains 20±5 wt % of shellac and 60±10 wt % of isopropyl alcohol and 5±10 wt % of hydroxypropyl cellulose and silica. The second wetness indicator ink is a responsive color composition that contains 3±1 wt % D&C red 27 and 60±10 wt % isopropyl alcohol. The third wetness indicator ink is the same varnish coating that is used at the first print station. The film is first printed with the varnish coating at a 3 g/sqm add-on weight and at a line speed of 100 m/min. The first varnish coating graphic design is printed on an area that is 20±5% larger than the graphic design that is printed with the second wetness indicator ink so that the varnish coating completely covers the wetness indicator ink graphic during the print process variation. The third wetness indicator ink, which is the additional varnish coating, is also printed on an area that is 20±5% larger than the graphic printed with the second wetness indicator ink. Therefore, the two varnish coating layers sandwich the second ink graphic.

This film is then dried and wound on to a roll and stored. At this time the printed varnish coating and responsive color composition graphic are completely invisible to naked eyes. This film is then incorporated into any one of the absorbent articles disclosed in U.S. Pat. Nos. 3,860,003, 4,636,207, 4,695,278, 4,704,115, 4,795,454, 4,900,317, 4,909,803 (Reissued as U.S. Pat. No. RE34920), U.S. Pat. Nos. 5,085,654, 5,492,751, 6,476,288, 6,627,787, 5,507,760, 5,609,587, 5,635,191, 5,643,588, 6,118,041, SIR H1630, U.S. Pat. Nos. 5,246,433, 5,769,838, 5,899,895, 5,899,896, and 6,120,487. Upon wetting of such an absorbent article, after about one minute an image begins to appear on the article's backsheet surface that faces the garment. After about 5 minutes, a bright pink image appears clearly.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
   a) a liquid pervious topsheet;
   b) a liquid impervious backsheet that is at least partially joined to the topsheet;
   c) an absorbent core disposed at least partially between the topsheet and the backsheet; and
   d) a wetness indicator printed onto a surface of said backsheet; the wetness indicator comprising a graphic that further comprises at least one hydrolyzable color composition and a varnish coating disposed adjacent to said hydrolyzable color composition; said graphic being invisible to the unaided eye;
   wherein upon wetting, said hydrolyzable color composition undergoes a hydrolytic reaction resulting in said invisible graphic becoming visible to the unaided eye.

2. The article of claim 1 wherein the color composition comprises:
   a) from about 1% to about 10%, by weight of the composition, of fluid dyestuffs; and
   b) from about 10% to about 99%, by weight of the composition, of a solvent.

3. The article of claim 2 wherein the solvent is a non-aqueous solvent selected from the group consisting of alcohols, acetates, and combinations thereof.

4. The article of claim 3 wherein said alcohol is selected from the group consisting of isopropyl alcohol, n-propyl alcohol, ethanol, methanol, and combinations thereof.

5. The article of claim 3 wherein said acetate is selected from the group consisting of isopropyl acetate, n-propyl acetate, and combinations thereof.

6. The article of claim 1 wherein said varnish coating comprises materials selected from the group consisting of acrylic copolymers, shellac-based acrylic resins, polyamides, and combinations thereof.

7. The article of claim 1 wherein said wetness indicator is printed on an inner surface.

8. The article of claim 1 wherein said varnish coating is disposed over said hydrolysable color composition.

9. The article of claim 1 wherein said varnish coating is disposed beneath said hydrolyzable color composition.

10. The article of claim 8 wherein said varnish coating is further disposed beneath said hydrolyzable color composition.

11. A method of printing a wetness indicator onto an absorbent article:
   a) providing an absorbent article wherein said article comprises a topsheet, a backsheet and an absorbent core;
   b) disposing between said backsheet and said absorbent core via printing a wetness indicator onto a surface of said backsheet; the wetness indicator comprising a graphic that further comprises at least one hydrolyzable color composition and a varnish coating disposed adjacent to said hydrolyzable color composition; said graphic being invisible to the unaided eye;
wherein upon wetting, said hydrolyzable color composition undergoes a hydrolytic reaction resulting in said invisible graphic becoming visible to the unaided eye.

12. The article of claim 1 wherein the backsheet is either breathable or non-breathable.

13. The article of claim 2 wherein the fluid dyestuff is selected from the group consisting of D&C Red 27, D&C Orange 5 and combinations thereof.

14. A disposable absorbent article comprising:
   a) a liquid pervious topsheet;
   b) a liquid impervious backsheet that is at least partially joined to the topsheet;
   c) an absorbent core disposed at least partially between the topsheet and the backsheet; and
   d) a wetness indicator printed onto a surface of said backsheet; the wetness indicator comprising a graphic that further comprises at least one hydrolyzable color composition; a first varnish coating disposed over said hydrolyzable color composition; and a second varnish coating disposed beneath said hydrolyzable color composition; said graphic being invisible to the unaided eye;
wherein upon wetting, said hydrolyzable color composition undergoes a hydrolytic reaction forming a carboxylic acid, resulting in said invisible graphic becoming visible to the unaided eye.

15. The article of claim 14 wherein the backsheet is either breathable or non-breathable.

16. The article of claim 1 wherein said chemical reaction forms a carboxylic acid.

* * * * *